United States Patent
Ashida et al.

(10) Patent No.: US 11,033,468 B2
(45) Date of Patent: Jun. 15, 2021

(54) LIQUID DISPERSION AND USES THEREOF

(71) Applicant: SAKAI CHEMICAL INDUSTRY CO., LTD., Sakai (JP)

(72) Inventors: Takuro Ashida, Osaka (JP); Koichiro Magara, Fukushima (JP); Akifumi Sano, Fukushima (JP); Ayana Shike, Fukushima (JP)

(73) Assignee: SAKAI CHEMICAL INDUSTRY CO., LTD., Osaka (JP)

( * ) Notice: Subject to any disclaimer, the term of this patent is extended or adjusted under 35 U.S.C. 154(b) by 0 days.

(21) Appl. No.: 16/097,785

(22) PCT Filed: Apr. 5, 2017

(86) PCT No.: PCT/JP2017/014291
§ 371 (c)(1),
(2) Date: Oct. 30, 2018

(87) PCT Pub. No.: WO2017/203846
PCT Pub. Date: Nov. 30, 2017

(65) Prior Publication Data
US 2020/0138677 A1 May 7, 2020

(30) Foreign Application Priority Data

May 27, 2016 (JP) .............................. JP2016-106448

(51) Int. Cl.
| | |
|---|---|
| *A61K 8/02* | (2006.01) |
| *A61K 8/04* | (2006.01) |
| *A61K 8/29* | (2006.01) |
| *A61K 8/55* | (2006.01) |
| *A61Q 1/10* | (2006.01) |

(52) U.S. Cl.
CPC ................ *A61K 8/022* (2013.01); *A61K 8/04* (2013.01); *A61K 8/29* (2013.01); *A61K 8/553* (2013.01); *A61K 2800/10* (2013.01); *A61Q 1/10* (2013.01)

(58) Field of Classification Search
CPC . A61K 8/022; A61K 8/04; A61K 8/29; A61K 8/553; A61K 2800/10; A61Q 1/10
See application file for complete search history.

(56) References Cited

U.S. PATENT DOCUMENTS

| | | | |
|---|---|---|---|
| 2009/0071368 A1* | 3/2009 | Steingrover | ............ C09C 3/12 106/35 |
| 2014/0199251 A1 | 7/2014 | Ashida | |
| 2016/0303032 A1* | 10/2016 | Kamei | ................... A61K 8/89 |
| 2017/0165154 A1 | 6/2017 | Ashida | |

FOREIGN PATENT DOCUMENTS

| | | | |
|---|---|---|---|
| EP | 1 829 524 | 9/2007 | |
| EP | 3 205 329 | 8/2017 | |
| JP | 06-032991 | 2/1994 | |
| JP | 2002-080771 | 3/2002 | |
| JP | 2007-119741 | 5/2007 | |
| JP | 2010-100580 | 5/2010 | |
| JP | 2010-184885 | 8/2010 | |
| JP | 2010-195694 | 9/2010 | |
| JP | 2012-097259 | 5/2012 | |
| JP | 2014-088374 | 5/2014 | |
| JP | 2014-097942 | 5/2014 | |
| JP | 2014-205628 | 10/2014 | |
| JP | 2015-117190 | 6/2015 | |
| JP | 2016-074660 | 5/2016 | |
| JP | 2016-199509 | 12/2016 | |
| WO | 2011/137212 | 11/2011 | |
| WO | 2013/018827 | 2/2013 | |
| WO | WO-2015093258 A1 * | 6/2015 | ............... A61K 8/89 |
| WO | 2015/125622 | 8/2015 | |
| WO | 2016/056589 | 4/2016 | |

OTHER PUBLICATIONS

Liu Guoji, "New Technology in the Modern Coating Process", China Light Industry Press, Ltd., Apr. 30, 2000, pp. 291-292, w/partial translation.

* cited by examiner

*Primary Examiner* — Robert A Wax
*Assistant Examiner* — Olga V. Tcherkasskaya
(74) *Attorney, Agent, or Firm* — Hamre, Schumann, Mueller & Larson, P.C.

(57) ABSTRACT

The present invention provides a liquid dispersion capable of stably maintaining the dispersed state for a long time and suitably applicable to both O/W type cosmetic products and W/O type cosmetic products. The present invention also provides a cosmetic raw material containing the liquid dispersion and a cosmetic product containing the liquid dispersion. The present invention provides a liquid dispersion containing a polyol (A); a nonionic surfactant (B); and a hydrophobized inorganic powder (C), wherein the water content in 100% by mass of the liquid dispersion is 1% by mass or less.

7 Claims, No Drawings

LIQUID DISPERSION AND USES THEREOF

CROSS-REFERENCE TO RELATED APPLICATIONS

This application claims priority to Japanese Patent Application No. 2016-106448.

TECHNICAL FIELD

The present invention relates to liquid dispersions and uses thereof. More specifically, the present invention relates to a liquid dispersion containing a hydrophobized inorganic powder, a cosmetic raw material containing the liquid dispersion, and a cosmetic product containing the liquid dispersion.

BACKGROUND ART

Inorganic powder is used as a colorant, filler, or the like in various applications. For example, pigment grade titanium oxide or iron oxide is suitably used as a color pigment for cosmetic products and coating materials. Such inorganic powder is known to be used in the form of a dispersion in which the inorganic powder is dispersed in a dispersion medium to facilitate good color development. In addition, techniques to provide a dispersion of surface-treated inorganic powder have been developed to render the inorganic powder water resistant against sweat, rain, and the like because the inorganic powder has a hydrophilic surface.

SUMMARY OF INVENTION

Technical Problem

Dispersing inorganic powder in a dispersion medium requires an adequate facility and manpower. Thus, for example, use of the inorganic powder in high-mix low-volume production is disadvantageous in terms of cost. Dispersing also requires high level know-how. Therefore, it is desirable if raw material suppliers can supply inorganic powder as a liquid dispersion because it will simplify dispersing in a dispersion medium. Yet, inorganic powder, particularly inorganic powder having a large particle size compared to fine particles (for example, inorganic powder having a particle size of about 150 nm or more) easily settles in a dispersion medium, so that unfortunately, the dispersion stability is poor, and caking and phase separation (such as color separation) occur. It has been difficult to provide a stable liquid dispersion of the inorganic powder.

For an aqueous dispersion containing polyvinylpyrrolidone and a pigment having a particle size greater than 100 nm as measured by a laser particle size analyzer, there is still room for improvement to further increase the dispersion stability of the pigment to provide a stable liquid dispersion.

Dispersions in which an inorganic powder of organically surface-treated fine particles are dispersed in water can provide cosmetic products having fine texture, good handling properties, and excellent water and sweat repellency, and are particularly useful as cosmetic raw materials. Yet, these inorganic powders disclosed consist of fine particles. Thus, there is still room for improvement to increase the stability of a liquid dispersion of a pigment grade inorganic powder having, for example, an average particle size of 150 nm or more. In addition, there is also still room for improvement to enable the inorganic powder to further exhibit the effect not only when the inorganic powder is applied to O/W type cosmetic products (oil-in-water type cosmetic products) but also to W/O type cosmetic products (water-in-oil type cosmetic products).

The present invention is made in view of the current situation described above, and aims to provide a liquid dispersion capable of stably maintaining the dispersed state for a long time and suitably applicable to both O/W type cosmetic products and W/O type cosmetic products. The present invention also aims to provide a cosmetic raw material containing the liquid dispersion and a cosmetic product containing the liquid dispersion.

Solution to Problem

The present inventors focused on the fact that a liquid dispersion containing a polyol, a nonionic surfactant, and a hydrophobized inorganic powder can provide a cosmetic product having good color development, fine texture, good handling properties, and excellent water and sweat repellency. As a result of further studies, the present inventors found that when the liquid dispersion contains substantially no water (specifically, the water content in 100% by mass of the liquid dispersion is 1% by mass or less), the liquid dispersion immediately after its production has an adequate viscosity even when the liquid dispersion contains a hydrophobized inorganic powder having, for example, an average particle size of 150 nm or more. Thus, the liquid dispersion can stably maintain the dispersed state for a long time, and caking and phase separation which occur over time can be sufficiently reduced or prevented. This liquid dispersion can be easily stored and transported in the form of the dispersion, and dispersing the liquid dispersion in a dispersion medium can be simplified or omitted. Thus, the liquid dispersion is useful as a versatile raw material, and is particularly useful as a cosmetic raw material. The liquid dispersion is also suitably applicable to both O/W type cosmetic products and W/O type cosmetic products. Thus, the present inventors successfully arrived at a solution to the above problem, and completed the present invention.

Specifically, the present invention provides a liquid dispersion containing a polyol (A); a nonionic surfactant (B); and a hydrophobized inorganic powder (C), wherein the water content in 100% by mass of the liquid dispersion is 1% by mass or less.

Preferably, the liquid dispersion further contains a lecithin and/or hydrogenated lecithin (D). This improves the adhesion of the hydrophobized inorganic powder (C) to the skin when used in a cosmetic product, for example, resulting in further improved usability such as improved makeup durability.

Preferably, the polyol (A) and the nonionic surfactant (B) are present at a mass ratio (A/B) of 70-95/30-5. This improves the dispersion of the hydrophobized inorganic powder (C).

Preferably, the hydrophobized inorganic powder (C) has an average particle size of 150 nm to 700 nm. Usually, such an inorganic powder having a pigment grade particle size easily settles. Thus, a liquid dispersion of the inorganic powder is considered to have poor dispersion stability, according to conventional common technical knowledge. However, contrary to the common technical knowledge, the liquid dispersion of the present invention has very good dispersion stability even when the liquid dispersion contains the hydrophobized inorganic powder (C) having such a particle size, and is thus particularly useful for use in color pigments.

Preferably, the hydrophobized inorganic powder (C) is an inorganic powder surface-treated with at least one selected from the group consisting of silicones, alkylsilanes, fatty acids or salts thereof, amino acids or salts thereof, and alkylphosphoric acids or salts thereof. This sufficiently blocks a hydrophilic moiety of the surface-treated inorganic powder. For example, when such a hydrophobized inorganic powder is added to a cosmetic product containing a water-soluble polymer, the formation of a gel between the hydrophobized inorganic powder (C) and the water-soluble polymer is suppressed. It also sufficiently reduces the rough feeling of the cosmetic product when in use and increases the water resistance.

Preferably, the polyol (A) is at least one selected from the group consisting of ethylene glycol, propylene glycol, dipropylene glycol, 1,3-butylene glycol, pentylene glycol, glycerol, diglycerol, triglycerol, and polyglycerol. This allows the nonionic surfactant (B) to be more uniformly applied to the surface of the hydrophobized inorganic powder (C), further stabilizing the liquid dispersion.

Preferably, the nonionic surfactant (B) is a polyether-modified silicone. This further improves the stability of the liquid dispersion and the feel of a cosmetic product containing the liquid dispersion, for example. The polyether-modified silicone is suitable also because of its high safety and high thermal stability.

Preferably, the liquid dispersion has a viscosity at 25° C. of 2000 mPa·s to 500000 mPa·s. This makes the hydrophobized inorganic powder (C) less flowable (i.e., less settleable), further improving the dispersion stability.

The present invention also relates to a cosmetic raw material containing the liquid dispersion.

The present invention also relates to a cosmetic product containing the liquid dispersion.

Advantageous Effects of Invention

The liquid dispersion of the present invention can stably maintain the dispersed state for a long time. Thus, dispersing the liquid dispersion in a dispersion medium can be simplified or omitted, which contributes to a reduction in the cost required for dispersing. The liquid dispersion can be used to provide a cosmetic product having good color development, fine texture, good handling properties, and excellent water and sweat repellency, and is thus particularly useful as a cosmetic raw material. In particular, the liquid dispersion is suitably applicable to both O/W type cosmetic products and W/O type cosmetic products.

DESCRIPTION OF EMBODIMENTS

An example of the present invention is specifically described below, but the present invention is not limited to the following description, and modifications can be made within the scope of the present invention.

(Liquid Dispersion)

The liquid dispersion of the present invention contains a polyol (A), a nonionic surfactant (B), and a hydrophobized inorganic powder (C). The total amount of these essential components is preferably 80% by mass or more relative to the total 100% by mass of the liquid dispersion. The total content is more preferably 85% by mass or more, still more preferably 90% by mass or more, particularly preferably 95% by mass or more, most preferably 97% by mass or more. The liquid dispersion may contain other components if necessary, and each component may be used alone or in combination of two or more kinds thereof.

The following describes the components.

Polyol (A)

The polyol (A) is not particularly limited as long as it is a dihydric or higher hydric alcohol. For example, a C1-C20 polyol is preferred. More preferably, the polyol (A) is at least one selected from the group consisting of ethylene glycol, propylene glycol, dipropylene glycol, 1,3-butylene glycol, pentylene glycol, glycerol, diglycerol, triglycerol, and polyglycerol. This allows the nonionic surfactant (B) to be more uniformly applied to the surface of the hydrophobized inorganic powder (C), further stabilizing the liquid dispersion. It is particularly preferred to use 1,3-butylene glycol. Use of 1,3-butylene glycol in a cosmetic product is particularly preferred because it is highly safe to human body.

The amount of the polyol (A) is preferably 10% by mass or more relative to the total 100% by mass of the liquid dispersion. This further improves the dispersion stability of the liquid dispersion. The amount of the polyol (A) is more preferably 15% by mass or more, still more preferably 20% by mass or more. The upper limit is not particularly limited, but it is preferably 50% by mass or less in order to improve the effect resulting from other components. The upper limit is more preferably 45% by mass or less, still more preferably 40% by mass or less.

Nonionic Surfactant (B)

The nonionic surfactant (B) is not particularly limited as long as it is a compound commonly used as a non-ionic surfactant. Examples include polyethers or derivatives thereof, polyether alkyl ethers, polyoxyalkylene alkenyl phenylethers, polyether fatty acid esters, sorbitan fatty acid esters, polyether sorbitan fatty acid esters, glycerol fatty acid esters, polyglycerol fatty acid esters, sucrose fatty acid esters, polyether castor oil, polyether hardened castor oil, polyether-modified silicones, and polyglycerol-modified silicones. In particular, it is preferred to use a polyether fatty acid ester, a polyether sorbitan fatty acid ester, and/or a polyether-modified silicone. It is more preferred to use at least a polyether-modified silicone. This further improves the stability of the liquid dispersion and the feel of a cosmetic product containing the liquid dispersion, for example. The polyether-modified silicone is also suitable because of its high safety and high thermal stability.

The nonionic surfactant (B) is also preferably a compound that dissolves to transparency or becomes slightly turbid at 35° C. when mixed at a concentration of 20% by mass with 1,3-butylene glycol (when the nonionic surfactant is in a paste state to a solid state at room temperature, the mixture is heated to provide a uniform mixture, and the state is observed at 35° C.). This enables efficient formation of a layer of the nonionic surfactant on the surface of the hydrophobized inorganic powder (C), further improving the dispersion stability of the liquid dispersion.

In the case where a mixture of two or more nonionic surfactants is used, the mixture preferably dissolves to transparency or becomes slightly turbid by the above test when the nonionic surfactants are present at a mixing ratio at which these nonionic surfactants are added to the liquid dispersion.

The nonionic surfactant (B) is also preferably a compound that is insoluble or becomes cloudy at 35° C. when mixed at a concentration of 20% by mass with water (when the nonionic surfactant is in a paste state to a solid state at room temperature, the mixture is heated to provide a uniform mixture, and the state is observed at 35° C.). This allows the liquid dispersion containing the nonionic surfactant (B) to be added as a cosmetic raw material to a cosmetic product without reducing its dispersibility in water, and the resulting cosmetic product has better water resistance.

In the case where a mixture of two or more nonionic surfactants is used, the mixture is preferably insoluble or becomes cloudy by the above test when the nonionic surfactants are present at a mixing ratio at which these nonionic surfactants are added to the liquid dispersion.

Herein, the expression "dissolves to transparency" means that the resultant mixture has a haze value lower than 10 at an optical path length of 10 mm at 35° C. The expression "becomes slightly turbid" means that the resultant mixture has a haze value of 10 or higher at an optical path length of 10 mm at 35° C., and has a total light transmittance of 30% or higher. The expression "insoluble" refers to a state where the mixture leaves undissolved residue, or even though the components are apparently mixed together, the mixture undergoes phase separation after one hour of mixing. The expression "becomes cloudy" means that the resultant mixture has a haze value of 10 or higher at an optical path length of 10 mm at 35° C., and has a total light transmittance lower than 30%.

Preferably, the nonionic surfactant (B) has a hydrophilic-lipophilic balance (HLB) of 6 to 12, for example. The HLB in this range further improves the dispersibility of the hydrophobized inorganic powder (C). In addition, it improves the adhesion of the hydrophobized inorganic powder (C) to the skin even when the liquid dispersion is added to an O/W type cosmetic product (oil-in-water type cosmetic product), and also improves the water resistance.

When a mixture of two or more nonionic surfactants (B) is used, preferably, the HLB of the mixture is in the above range.

Herein, the HLB is determined by the following formula defined by W. C. Grifinn.

$$N_{HLB}=(E+P)/5$$

wherein $N_{HLB}$ is an HLB value; E is a percentage (% by mass) of a polyether part of the nonionic surfactant (B) relative to all the molecules of the nonionic surfactant (B); and P is a percentage (% by mass) of a polyol part of the nonionic surfactant (B) relative to all the molecules of the nonionic surfactant (B).

The amount of the nonionic surfactant (B) is preferably set such that the polyol (A) and the nonionic surfactant (B) are present at a mass ratio (A/B) of 70-95/30-5. This improves the dispersion of the hydrophobized inorganic powder (C). In addition, the liquid dispersion of the present invention can adequately maintain the dispersion stability even with a reduced amount of the nonionic surfactant (B). Thus, it is possible to improve the stability of the liquid dispersion during use, with a reduced amount of the nonionic surfactant (B). From this point of view, the mass ratio (A/B) is more preferably 72-95/28-5, still more preferably 73-95/27-5.

Hydrophobized Inorganic Powder (C)

Preferably, the hydrophobized inorganic powder (C) has an average particle size of 150 nm to 700 nm. Usually, such an inorganic powder having a pigment grade particle size easily settles. Thus, a liquid dispersion of the inorganic powder is considered to have poor dispersion stability, according to conventional common technical knowledge. However, contrary to the common technical knowledge, the liquid dispersion of the present invention has very good dispersion stability even when the liquid dispersion contains the hydrophobized inorganic powder (C) having such a particle size, and is thus particularly useful for use in color pigments. In order to facilitate better color development, the average particle size is more preferably 180 nm or more, still more preferably 200 nm or more.

Herein, the average particle size of the inorganic powder is a value obtained by measuring the particle size of 200 particles randomly selected on a scanning electron microscope image (SEM image) and by calculating an average primary particle size. The individual primary particle size is calculated using the diameter of a minimum circumscribed circle.

The hydrophobized inorganic powder (C) may have any shape, such as a spherical shape (including a substantially spherical shape), a bar shape, an acicular shape, a fusiform shape, a plate shape, a hexagonal plate, or an amorphous shape; or the hydrophobized inorganic powder (C) may be in the form of an acicular aggregate.

The shape can be observed by a scanning electron microscope or the like.

The inorganic powder (also referred to as "raw material inorganic powder") of the hydrophobized inorganic powder (C) may be of any kind. Examples include titanium oxide, iron oxide, zinc oxide, cerium oxide, barium sulfate, calcium carbonate, silica, aluminum hydroxide, alumina, boron nitride, talc, mica, and kaolin. In particular, titanium oxide, iron oxide, zinc oxide, cerium oxide, and a composite thereof are preferred in order to make the liquid dispersion more useful for use in cosmetic products. It is more preferred to use titanium oxide and/or iron oxide. An adequate amount of titanium oxide and an adequate amount of iron oxide may be mixed together for the purpose of toning or the like.

The raw material inorganic powder may be a composite powder whose surface is covered with a different inorganic material. In this case, the composite powder is hydrophobized to be used as the hydrophobized inorganic powder (C). The different inorganic material is not particularly limited. Examples include zinc oxide, titanium oxide, cerium oxide, iron oxide, barium oxide, hydrous silicic acid, silica, aluminum hydroxide, alumina, and zirconia. The amount to be covered by any of these inorganic materials is, for example, preferably 0 to 25% by mass, more preferably 2 to 20% by mass, relative to the total 100% by mass of the inorganic powder after hydrophobization.

The hydrophobized inorganic powder (C) is a product obtained by hydrophobizing a raw material inorganic powder (which may be the composite powder). Hydrophobization is to treat the surface of a raw material inorganic powder with a hydrophobic organic surface treatment agent. Hydrophobization blocks a hydrophilic moiety on the target surface of the raw material inorganic powder, thus improving the water resistance and the water repellency. In addition, for example, when the hydrophobized inorganic powder is added to a cosmetic product containing a water-soluble polymer, the formation of a gel between the hydrophobized inorganic powder (C) and the water-soluble polymer is suppressed, and the rough feeling of the cosmetic product when in use is sufficiently reduced. Thus, the liquid dispersion containing the hydrophobized inorganic powder (C) is more useful for use in cosmetic products.

Here, the hydrophobized inorganic powder (C) preferably has a high degree of hydrophobicity. This can further increase the stability of the liquid dispersion. To measure the hydrophobicity, the hydrophobized inorganic powder is compacted into a flat plate having a uniform surface, and water (1 µL) is dropped onto the surface of the flat plate. The hydrophobicity can be determined based on the contact angle of the water droplet. The contact angle is preferably 45 degrees or more, more preferably 60 degrees or more, still more preferably 90 degrees or more.

The hydrophobic organic surface treatment agent is not particularly limited as long as it is an organic surface treatment agent commonly used for hydrophobization of particle surfaces, and it is preferably at least one selected from the group consisting of silicones, alkylsilanes, fatty acids or salts thereof, amino acids of salts thereof, and alkylphosphoric acids or salts thereof. This enhances the effect to be obtained by the hydrophobization, and sufficiently prevents separation of the treatment agent from the inorganic powder, further improving the dispersion stability.

The salt is not particularly limited. Preferred examples include metal salts, ammonium salts, and organic amine salts. Examples of metal atoms of the metal salts include monovalent metals such as sodium, lithium, potassium, rubidium, and cesium; divalent metals such as zinc, magnesium, calcium, strontium, and barium; trivalent metals such as aluminum; and other metals such as iron and titanium. Examples of organic amine groups of the organic amine salts include alkanolamine groups such as monoethanolamine, diethanolamine, and triethanolamine groups; alkyl amine groups such as monoethylamine, diethylamine, and triethylamine groups; and polyamine groups such as ethylenediamine and triethylenediamine groups. The salt is preferably an ammonium salt, a sodium salt, or a potassium salt, more preferably a sodium salt.

Preferred among the hydrophobic organic surface treatment agents is a silicone. Examples of the silicone include methyl hydrogen polysiloxane, dimethylpolysiloxane, a copolymer of methyl hydrogen polysiloxane and dimethylpolysiloxane, and organopolysiloxane containing a reactive trialkoxysilyl group such as a trimethoxysilyl group or a triethoxysilyl group.

Hydrophobization of the inorganic powder is preferably performed such that 0.1 to 10% by mass of the inorganic powder is hydrophobized relative to the total 100% by mass of the inorganic powder after hydrophobization (the hydrophobized inorganic powder (C)). The inorganic powder, which is hydrophobized to 0.1% by mass or more, has better water repellency and better water resistance. The effect of hydrophobization plateaus at 10% by mass. The inorganic powder is more preferably hydrophobized to 0.2 to 9% by mass, still more preferably to 0.5 to 8% by mass.

The amount of the hydrophobized inorganic powder (C) is preferably 40% by mass or more relative to the total 100% by mass of the liquid dispersion. With such a high concentration, the essential effect can be achieved with a small amount of the liquid dispersion when used as a versatile raw material. The concentration is more preferably 50% by mass or more, still more preferably 55% by mass or more, particularly preferably 60% by mass or more. In particular, in the case where titanium oxide is used as an inorganic powder, the concentration is furthermore preferably 60% by mass or more, particularly preferably 65% by mass or more, most preferably 70% by mass or more. The upper limit is not limited, but the concentration is preferably 95% by mass or less, more preferably 90% by mass or less, considering the amounts of other components.

Water

The liquid dispersion of the present invention contains substantially no water. The expression "contains substantially no water" means that the water content in 100% by mass of the liquid dispersion is 1% by mass or less. The liquid dispersion of the present invention can stably maintain the dispersed state for a long time although it contains substantially no water. That is, the present invention achieves an unusual effect that cannot be foreseen based on existing technical knowledge, and the present invention is also suitably applicable to both O/W type cosmetic products and W/O type cosmetic products. The water content in 100% by mass of the liquid dispersion is preferably less than 1% by mass, more preferably 0.8% by mass or less, still more preferably 0.5% by mass or less, particularly preferably 0.3% by mass or less, most preferably 0.2% by mass or less.

Herein, the water content in the liquid dispersion includes not only water as one of the components but also impurities (for example, water as an impurity in each component), In other words, the water content in the liquid dispersion is determined by the total value of the amount of water added and preliminary fed and the amount of water inherently present in each component. The water content in each component is measured by the Karl Fischer titration method as described in the later-described examples.

Lecithin and/or Hydrogenated Lecithin (D)

Preferably, the liquid dispersion of the present invention further contains a lecithin and/or hydrogenated lecithin (D). The presence of the lecithin and/or hydrogenated lecithin (D) improves the adhesion of the hydrophobized inorganic powder (C) to the skin, improving the makeup durability.

The lecithin and/or hydrogenated lecithin may be collectively referred to as "(hydrogenated) lecithin".

The amount of the lecithin and/or hydrogenated lecithin (D) (the total amount in the case where two kinds are used) is preferably 0.01 to 10 parts by mass relative to the total 100 parts by mass of the hydrophobized inorganic powder (C). If the amount is less than 0.01 parts by mass, the adhesion is unlikely to improve much. If the amount is more than 10 parts by mass, problems such as stickiness may occur. The amount is more preferably 0.1 to 8 parts by mass, still more preferably 0.5 to 5 parts by mass, particularly preferably 0.5 to 3 parts by mass.

Other Components

The liquid dispersion of the present invention may contain other components if necessary, in addition to the polyol (A), the nonionic surfactant (B), the hydrophobized inorganic powder (C), and the lecithin and/or hydrogenated lecithin (D) described above. The other components are not particularly limited, and examples include paraoxybenzoic acid alkylesters, benzoic acid, sodium benzoate, sorbic acid, potassium sorbate, phenoxyethanol, salicylic acid, carbolic acid, sorbic acid, parachloromethacresol, hexachlorophene, benzalkonium chloride, chlorhexidine chloride, photosensitizers, and antimicrobial preservatives and antibacterial agents such as phenoxyethanol.

The total amount of the other components is preferably 20% by mass or less relative to the total 100% by mass of the liquid dispersion, for example. The total amount is more preferably 15% by mass or less, still more preferably 10% by mass or less, particularly preferably 5% by mass or less.

The method for producing the liquid dispersion of the present invention is not particularly limited. The liquid dispersion may be produced by mixing the components described above. The mixing method is also not limited. Any common method that enables uniform dispersion may be used. For example, a disperser such as a bead mill, jet mill, or high pressure homogenizer may be used. Yet, the liquid dispersion of the present invention can be easily produced using a simple stirrer, without the need of such an expensive disperser. Thus, an expensive disperser such as a bead mill is advantageously dispensed with.

Preferably, the liquid dispersion of the present invention has a viscosity at 25° C. of 2000 mPa·s to 500000 mPa·s. The viscosity in this range makes the hydrophobized inorganic powder (C) less flowable (i.e., less settleable), further improving the dispersion stability. This effect is prominent particularly when the hydrophobized inorganic powder (C) has an average particle size of 150 nm or more, and the increase in viscosity over time is more sufficiently suppressed, improving the dispersion stability. The upper limit of the viscosity is more preferably 300000 mPa·s or less, still more preferably 100000 mPa·s or less, particularly preferably 50000 mPa·s or less. The lower limit of the viscosity is more preferably 3000 mPa·s or more, still more preferably 5000 mPa·s or more, particularly preferably 7000 mPa·s or more, most preferably 8000 mPa·s or more.

The "viscosity at 25° C." is the viscosity of the liquid dispersion containing only the polyol (A), the nonionic surfactant (B), the hydrophobized inorganic powder (C), and the lecithin and/or hydrogenated lecithin (D) but no other components. Such a liquid dispersion is produced, left to stand at 40° C. for one day, and then cooled to 25° C. to measure the viscosity by a B-type viscometer (LVDV1M produced by EKO Instruments) (measurement temperature: 25° C.).

(Use)

The liquid dispersion of the present invention can stably maintain the dispersed state for a long time. Thus, the liquid dispersion can be easily stored and transported in the form of the dispersion, and dispersing the liquid dispersion in a dispersion medium can be simplified or omitted. Therefore, the liquid dispersion is useful as a versatile raw material, and is particularly useful as a cosmetic raw material, a coating raw material, or an ink raw material. In particular, the liquid dispersion of the present invention can be used to provide a cosmetic product having good color development, fine texture, good handling properties, and excellent water and sweat repellency, and is thus particularly useful as a cosmetic raw material. A cosmetic raw material containing the liquid dispersion of the present invention is encompassed by the present invention. A cosmetic product, a coating composition, and an ink composition each containing the liquid dispersion of the present invention are also encompassed by the invention achieved by the present inventors. Among these, the cosmetic product is described below in further detail.

(Cosmetic Product)

The cosmetic product of the present invention contains the liquid dispersion of the present invention. The production method of such a cosmetic product is not particularly limited, and any common cosmetic production method may be used.

The cosmetic product is not particularly limited. Examples include skin care products, hair products, makeup products, and UV protection products. The form of the cosmetic product is also not particularly limited. Examples include liquid, emulsion, cream, solid, paste, gel, multilayer, foam, and spray forms.

The cosmetic product may also be any of the following products: oil-based cosmetic products, water-based cosmetic products, O/W type cosmetic products (oil-in-water type cosmetic products), and W/O type cosmetic products (water-in-oil type cosmetic products). In other words, the liquid dispersion of the present invention is suitably applicable to any of these products. Among these products, the liquid dispersion is particularly suitably applicable to both O/W type cosmetic products and W/O type cosmetic products. A preferred O/W type cosmetic product is one that is used in combination with an anionic water-soluble polymer. In this case, use of the liquid dispersion of the present invention improves the water resistance of the cosmetic product without reducing the viscosity or causing gelation, for example, even when the liquid dispersion is used in combination with an anionic water-soluble polymer. The liquid dispersion used in a W/O type cosmetic product can improve the adhesion of the pigment to the skin due to water evaporation after the W/O type cosmetic product is applied to the skin, improving the makeup durability. In particular, addition of lecithin or hydrogenated lecithin, for example, significantly improves the adhesion to the skin.

The cosmetic product may contain one or more aqueous components and oily components of any kinds which are commonly used in the cosmetic field, if necessary. The aqueous components and the oily components are not particularly limited. Examples include oil agents, surfactants, humectants, higher alcohols, sequestrants, natural or synthetic polymers, water-soluble or oil-soluble polymers, UV screening agents, various extracts, pharmaceutical components, coloring material (such as dyes and pigments), preservatives, antioxidants, colorants, thickeners, pH regulators, perfumes, cooling sensation agents, antiperspirants, antiseptics, skin activators, and various powders.

EXAMPLES

The following examples are provided to describe the present invention in detail, but the present invention is not limited to these examples. The percent (%) and parts mean "percent by mass (percent by weight)" and parts by mass (parts by weight), respectively, unless otherwise specified.

Various physical properties were evaluated as follows.

1. Water Content in Each Component (Karl Fischer Titration)

(1) Water Content in Inorganic Powder

Methanol was placed in a titration cell, and the titration cell was set in a water evaporator ("Evaporator EV-2000" produced by Hiranuma Sangyo Co., Ltd.). After a blank test, a sample (0.5 g) was fed to the titration cell. Heating was maintained for 10 minutes, and the water content was measured using a water content measuring device ("Aqua Counter AQV-2200" produced by Hiranuma Sangyo Co., Ltd.).

(2) Water Content in Oil (Raw Materials Other than the Inorganic Powder)

Methanol was placed in a titration cell. After a blank test, a sample (0.5 g) was fed to the titration cell. The water content was measured using a water content measuring device ("Aqua Counter AQV-2200" produced by Hiranuma Sangyo Co., Ltd.).

2. Viscosity

The liquid dispersion was left to stand at 40° C. for one day or one week after production, and then cooled to 25° C. The viscosity was measured with a B-type viscometer (LVDV1M produced by EKO Instruments) (measurement temperature: 25° C.)

3. Caking and Supernatant

The liquid dispersion was left to stand at 40° C. after production, and visually observed after one week of standing.

In the table, those with caking or supernatant are indicated with "Present", and those without caking or supernatant are indicated with "Absent".

4. Particle Size (1) Particle Size Distribution

The liquid dispersion containing a white inorganic powder was diluted with water, and then the median diameter $D_{50}$ was measured using "LA-950" produced by Horiba, Ltd.

(2) Fineness-of-Grind Gauge

A liquid dispersion containing a colored inorganic powder was measured with a 50-μm fineness-of-grind gauge in accordance with JIS K5600 (1999).

Example 1

The following components were added in sequence to a metal beaker in the amounts shown in Table 1: 1,3-butylene glycol (Daicel Corporation), a nonionic surfactant ("KF-6013" produced by Shin-Etsu Chemical Co., polyether-modified silicone), and titanium oxide ("MKR-1S" produced by Sakai Chemical Industry Co., Ltd., titanium oxide 98.5%, hydrogen dimethicone 1.5%, average particle size: 200 nm). At each time of addition, the components were blended in with a metal spatula and mixed together with a mixer. The thus-obtained liquid dispersion was evaluated as described above. Table 1 shows the results.

Example 2

A liquid dispersion was produced in the same manner as in Example 1, except that the amounts of the components were changed as shown in Table 1. The liquid dispersion was evaluated as described above. Table 1 shows the results.

Example 3

A liquid dispersion was produced in the same manner as in Example 1, except that the average particle size of the titanium oxide was changed to 500 nm. The liquid dispersion was evaluated as described above. Table 1 shows the results.

Example 4

A liquid dispersion was produced in the same manner as in Example 1, except that iron oxide (yellow) ("SI-Yellow LL-100P LHC" produced by Miyoshi Kasei, Inc., treated with hydrogen dimethicone, average particle size: 700 nm) was used instead of titanium oxide and that the amounts of the components were changed as shown in Table 1. The liquid dispersion was evaluated as described above. Table 1 shows the results.

Example 5

A liquid dispersion was produced in the same manner as in Example 1, except that iron oxide (red) ("SI-Red R-516PS LHC" produced by Miyoshi Kasei, Inc., treated with hydrogen dimethicone, average particle size: 700 nm) was used instead of titanium oxide and that the amounts of the components were changed as shown in Table 1. The liquid dispersion was evaluated as described above. Table 1 shows the results.

Example 6

A liquid dispersion was produced in the same manner as in Example 1, except that iron oxide (black) ("SI-Black BL-100P LHC" produced by Miyoshi Kasei, Inc., treated with hydrogen dimethicone, average particle size: 300 nm) was used instead of titanium oxide and that the amounts of the components were changed as shown in Table 1. The liquid dispersion was evaluated as described above. Table 1 shows the results.

Example 7

The following components were added in sequence to a metal beaker in the amounts shown in Table 1: 1,3-butylene glycol (Daicel Corporation), a nonionic surfactant ("KF-6013" produced by Shin-Etsu Chemical Co., polyether-modified silicone), lecithin ("Lecithin CL" produced by J-Oil Mills, Inc.), and titanium oxide ("MKR-1S" produced by Sakai Chemical Industry Co., Ltd., titanium oxide 98.5%, hydrogen dimethicone 1.5%, average particle size: 200 nm). At each time of addition, the components were blended in with a metal spatula and mixed together with a mixer. The thus-obtained liquid dispersion was evaluated as described above. Table 1 shows the results.

Example 8

The following components were mixed together: 60.1 g of titanium oxide ("MKR-1S" produced by Sakai Chemical Industry Co., Ltd., titanium oxide 98.5%, hydrogen dimethicone 1.5%, average particle size: 200 nm), 2.6 g of iron oxide (yellow) ("SI-Yellow LL-100P LHC" produced by Miyoshi Kasei, Inc., treated with hydrogen dimethicone, average particle size: 700 nm), 0.7 g of iron oxide (black) ("SI-Black BL-100P LHC" produced by Miyoshi Kasei, Inc., treated with hydrogen dimethicone, average particle size: 300 nm), and 7.8 g of iron oxide (red) ("SI-Red R-516PS LHC" produced by Miyoshi Kasei, Inc., treated with hydrogen dimethicone, average particle size: 700 nm). Thus, a hydrophobized inorganic powder matched to the skin tone was obtained.

The following components were added in sequence to a metal beaker in the amounts shown in Table 1: 1,3-butylene glycol (Daicel Corporation), a nonionic surfactant ("KF-6013", polyether-modified silicone produced by Shin-Etsu Chemical Co.), and the hydrophobized inorganic powder matched to the skin tone. At each time of addition, the components were blended in with a metal spatula and mixed together with a mixer. The thus-obtained liquid dispersion was evaluated as described above. Table 1 shows the results.

Comparative Example 1

An attempt was made to produce a liquid dispersion in the same manner as in Example 1, except that no nonionic surfactant was used and that the amounts of the components were changed as shown in Table 1, but the inorganic powder did not disperse. Thus, no liquid dispersion was obtained.

Comparative Example 2

The following components were added in sequence to a metal beaker in the amounts shown in Table 1: 1,3-butylene glycol (Daicel Corporation), a nonionic surfactant ("KF-6013" produced by Shin-Etsu Chemical Co., polyether-modified silicone), titanium oxide ("MKR-1S" produced by Sakai Chemical Industry Co., Ltd., titanium oxide 98.5%, hydrogen dimethicone 1.5%, average particle size: 200 nm), and water. At each time of addition, the components were blended in with a metal spatula manually. The thus-obtained liquid dispersion was evaluated as described above. Table 1 shows the results.

The water content in 100% by mass of each component was as follows, as measured by the Karl Fischer titration method. Titanium oxide having an average particle size of 200 nm: 0.126% by mass Titanium oxide having an average particle size of 500 nm: 0.103% by mass
Iron oxide (red): 0.130% by mass
Iron oxide (yellow): 0.487% by mass
Iron oxide (black): 0.061% by mass
1,3-Butylene glycol: 0.262% by mass
Nonionic surfactant (KF-6013): 0.272% by mass
Lecithin: 0.186% by mass

TABLE 1

| | | Example 1 | Example 2 | Example 3 | Example 4 | Example 5 |
|---|---|---|---|---|---|---|
| Hydrophobized inorganic powder (C) | Type of inorganic powder | Titanium oxide | Titanium oxide | Titanium oxide | Iron oxide (yellow) | Iron oxide (red) |
| | Average particle size (SEM diameter) (nm) | 200 | 200 | 500 | 700 | 700 |
| Composition Unit: g | (A): 1,3-bg | 22 | 22 | 22 | 37 | 37 |
| | (B): nonionic surfactant (KF-6103) | 3 | 8 | 3 | 3 | 3 |
| | (C): hydrophobed inorganic powder | 75 | 70 | 75 | 60 | 60 |
| | (D): (hydrogenated) lecithin | — | — | — | — | — |
| | Water | — | — | — | — | — |
| | Water content (%) in dispersion | 0.16 | 0.17 | 0.14 | 0.4 | 0.18 |
| Evaluation | Viscosity at day 1 (mPa·s) | 15600 | 10250 | 8900 | 10750 | 18000 |
| | Viscosity at week 1 (mPa·s) | 15800 | 14400 | 8500 | 12550 | 19500 |
| | Supernatant | Absent | Absent | Absent | Absent | Absent |
| | Caking | Absent | Absent | Absent | Absent | Absent |
| particle size | $D_{50}$ (nm) | 429 | 422 | 768 | — | — |
| | Fineness-of-grind gauge | — | — | — | 5 μm or less | 5 μm or less |

| | | Example 6 | Example 7 | Example 8 | Comparative Example 1 | Comparative Example 2 |
|---|---|---|---|---|---|---|
| Hydrophobized inorganic powder (C) | Type of inorganic powder | Iron oxide (black) | Titanium oxide | Titanium oxide Iron oxide (yellow) Iron oxide (black) Iron oxide (red) | Titanium oxide | Titanium oxide |
| | Average particle size (SEM diameter) (nm) | 300 | 200 | — | 200 | 200 |
| Composition Unit: g | (A): 1,3-bg | 37 | 20.5 | 25.8 | 25 | 7.5 |
| | (B): nonionic surfactant (KF-6103) | 3 | 3 | 3 | — | 7.5 |
| | (C): hydrophobed inorganic powder | 60 | 75 | 71.2 | 75 | 70 |
| | (D): (hydrogenated) lecithin | — | 1.5 | — | — | — |
| | Water | — | — | — | — | 15 |
| | Water content (%) in dispersion | 0.14 | 0.16 | 0.17 | 0.16 | 15.13 |
| Evaluation | Viscosity at day 1 (mPa·s) | 31650 | 16020 | 18210 | Unmeasurable | 21750 |
| | Viscosity at week 1 (mPa·s) | 30950 | 16680 | 18850 | — | Off-scale high |
| | Supernatant | Absent | Absent | Absent | — | Absent |
| | Caking | Absent | Absent | Absent | — | Absent |
| particle size | $D_{50}$ (nm) | — | 420 | — | — | 487 |
| | Fineness-of-grind gauge | 5 μm or less | — | 5 μm or less | — | — |

Table 1 shows the following results.

In each of Examples 1 to 6 and 8, the liquid dispersion contains the polyol (A), the nonionic surfactant (B), and the hydrophobized inorganic powder (C). In Example 7, the liquid dispersion further contains the lecithin and/or hydrogenated lecithin (D), and the water content in 100% by mass of the liquid dispersion is 1% by mass or less. In this case, the liquid dispersion had a stable viscosity over time, and the formation of supernatant and caking was suppressed. In Examples 1 to 3 and 7, the liquid dispersion had a small median diameter $D_{50}$, and the hydrophobized inorganic powder (C) adequately dispersed. In Examples 4 to 6 and 8, no coarse particles were found when measured by the fineness-of-grind gauge.

The liquid dispersion obtained in each of Examples 1 to 8 was capable of being stably added not only to O/W type cosmetic products (oil-in-water type cosmetic products) but also to W/O type cosmetic products (water-in-oil type cosmetic products).

In contrast, in Comparative Example 1 in which no nonionic surfactant (B) was used, the inorganic powder did not disperse, and no liquid dispersion was thus obtained. Although not tabulated, a case where polyvinylpyrrolidone was used instead of the nonionic surfactant in Example 1 was also examined. Also in this case, the inorganic powder did not disperse, and no liquid dispersion was obtained. In Comparative Example 2, water was used as a component. In this case, when the resultant liquid dispersion was added to a W/O type cosmetic product (water-in-oil type cosmetic product) and left to stand at 50° C. for one week, the liquid dispersion underwent phase separation and had poor stability. In addition, the liquid dispersion obtained in Comparative Example 2 was a liquid with fluidity at first, but after one week of the production, the liquid dispersion was in a significantly low fluidity state (solidified).

The above shows that the liquid dispersion containing the polyol (A), the nonionic surfactant (B), the hydrophobized inorganic powder (C), and the lecithin and/or hydrogenated lecithin (D) can stably maintain the dispersed state for a long time only when the water content in 100% by mass of the liquid dispersion is 1% by mass or less, and that such a liquid dispersion is suitably applicable to both O/W type cosmetic products and W/O type cosmetic products.

Preparation Example

Example 9 (O/W Foundation)

An O/W foundation was obtained by the following production method using the components shown in the following Table 2.
(Production Method)
(1) Components 15 to 18 were uniformly mixed with a portion of Component 19.
(2) Components 1 to 7 were uniformly mixed together and heated.
(3) Components 8 to 14 and the rest of Component 19 were uniformly mixed together and heated.
(4) The mixture (2) was added to the mixture (3) and emulsified. The resultant emulsion was cooled and blended with the mixture (1). Thus, an O/W foundation was obtained.

TABLE 2

| Components | Amount (% by mass) |
|---|---|
| 1. Stearic acid | 0.7 |
| 2. Behenyl alcohol | 0.5 |
| 3. Glyceryl stearate (SE) | 0.5 |
| 4. Squalane | 5.0 |
| 5. Ethylhexyl methoxycinnamate | 4.0 |
| 6. Sorbitan sesquiisostearate | 0.5 |
| 7. Isotridecyl isononanoate | 5.0 |
| 8. Carbomer | 0.3 |
| 9. (Acrylates/alkyl acrylate (C10-C30)) cross polymer | 0.1 |
| 10. Xanthan gum (2% aq) | 2.0 |
| 11. Stearoyl glutamic acid Na | 0.02 |
| 12. Polysorbate 80 | 1.0 |
| 13. Triethanolamine | 0.75 |
| 14. 1,3-Butylene glycol | 7.0 |
| 15. Liquid dispersion of titanium oxide (Example 2) | 10.0 |
| 16. Liquid dispersion of iron oxide (yellow) (Example 4) | 1.63 |
| 17. Liquid dispersion of iron oxide (red) (Example 5) | 0.55 |
| 18. Liquid dispersion of iron oxide (black) (Example 6) | 0.2 |
| 19. Water | 60.25 |

The thus-obtained O/W foundation in Example 9 was stable without time-dependent changes, and the feel of the O/W foundation was smooth with good spreadability on the skin when the O/W foundation was applied. The O/W foundation left no sticky or rough feeling on the skin, and exhibited excellent makeup durability.

Example 10 (O/W Foundation)

An O/W foundation was obtained by the following production method using the components shown in the following Table 3.
(Production Method)
(1) Components 16 to 19 were uniformly mixed with a portion of Component 20.
(2) Components 1 to 8 were uniformly mixed together and heated.
(3) Components 9 to 15 and the rest of Component 20 were uniformly mixed together and heated.
(4) The mixture (2) was added to the mixture (3) and emulsified. The resultant emulsion was cooled and blended with the mixture (1). Thus, an O/W foundation was obtained.

TABLE 3

| Components | Amount (% by mass) |
|---|---|
| 1. Stearic acid | 0.7 |
| 2. Behenyl alcohol | 0.5 |
| 3. Glyceryl stearate (SE) | 0.5 |
| 4. Squalane | 8.0 |
| 5. Tri(caprylic acid/capric acid)glycerol | 2.0 |
| 6. Sorbitan sesquiisostearate | 0.5 |
| 7. Zinc oxide dispersion in oil (note 1) | 5.0 |
| 8. Titanium oxide dispersion in oil (note 2) | 10.0 |
| 9. Carbomer | 0.3 |
| 10. (Acrylates/alkyl acrylate (C10-C30)) cross polymer | 0.1 |
| 11. Xanthan gum (2% aq) | 2.0 |
| 12. Stearoyl glutamic acid Na | 0.02 |
| 13. Polysorbate 80 | 1.0 |
| 14. Triethanolamine | 0.75 |
| 15. 1,3-Butylene glycol | 7.0 |
| 16. Liquid dispersion of titanium oxide (Example 1) | 10.0 |
| 17. Liquid dispersion of iron oxide (yellow) (Example 4) | 1.63 |
| 18. Liquid dispersion of iron oxide (red) (Example 5) | 0.55 |
| 19. Liquid dispersion of iron oxide (black) (Example 6) | 0.2 |
| 20. Water | 49.25 |

(note 1)
Zinc oxide dispersion in oil: DIF-TL-3W (Sakai Chemical Industry Co., Ltd.)
(note 2)
Titanium oxide dispersion in oil: DIS-TL-10A (Sakai Chemical Industry Co., Ltd.)

The thus-obtained O/W foundation in Example 10 was stable without time-dependent changes, and the feel of the O/W foundation was smooth with good spreadability on the skin when the O/W foundation was applied. The O/W foundation left no sticky or rough feeling on the skin, and exhibited excellent makeup durability with an UV protection effect.

Example 11 (O/W Foundation)

An O/W foundation was obtained by the following production method using the components shown in the following Table 4.
(Production Method)
(1) Components 11 to 14 were uniformly mixed with a portion of Component 17.
(2) Components 1 to 6 were uniformly mixed together and heated.
(3) Components 7 to 10 and the rest of Component 17 were uniformly mixed together and heated.
(4) The mixture (2) was added to the mixture (3) and emulsified. The resultant emulsion was cooled and blended with Components 15, 16, and the mixture (1). Thus, an O/W foundation was obtained.

TABLE 4

| Components | Amount (% by mass) |
|---|---|
| 1. Isotridecyl isononanoate | 8.0 |
| 2. Behenyl alcohol | 0.7 |
| 3. Glyceryl stearate (SE) | 0.7 |
| 4. Squalane | 6.0 |
| 5. Tri(caprylic acid/capric acid)glycerol | 3.0 |
| 6. Sorbitan sesquiisostearate | 0.5 |
| 7. (Acrylic acid Na/acryloyldimethyltaurine Na) copolymer (note 3) | 1.2 |
| 8. Hydroxyethyl cellulose (2% aq) | 2.0 |
| 9. PEG-20 sorbitan isostearate | 1.5 |
| 10. 1,3-Butylene glycol | 5.0 |
| 11. Liquid dispersion of titanium oxide (Example 7) | 10.0 |
| 12. Liquid dispersion of iron oxide (yellow) (Example 4) | 1.65 |
| 13. Liquid dispersion of iron oxide (red) (Example 5) | 0.55 |
| 14. Liquid dispersion of iron oxide (black) (Example 6) | 0.2 |
| 15. Zinc oxide dispersion in water (note 4) | 10.0 |
| 16. Titanium oxide dispersion in water (note 5) | 10.0 |
| 17. Water | 39.0 |

(note 3)
(Acrylic acid Na/acryloyldimethyltaurine Na) copolymer: SIMULGEL EG (SEPPIC)
(note 4)
Zinc oxide dispersion in water: DIF-AB-33W (Sakai Chemical Industry Co., Ltd.)
(note 5)
Titanium oxide dispersion in water: DIS-AB-10W (Sakai Chemical Industry Co., Ltd.)

The thus-obtained O/W foundation in Example 11 was stable without time-dependent changes, and the feel of the O/W foundation was smooth with good spreadability on the skin when the O/W foundation was applied. The O/W foundation left no sticky or rough feeling on the skin, and exhibited highly excellent makeup durability with a high UV protection effect.

Example 12 (W/O Foundation)

An W/O foundation was obtained by the following production method using the components shown in the following Table 5.
(Production Method)
(1) Components 8 to 11 were uniformly mixed with a portion of Component 15.
(2) Components 1 to 7 were uniformly mixed together.
(3) Components 12 to 14 and the rest of Component 15 were uniformly mixed together, and blended with the mixture (1).
(4) The mixture (3) was added to the mixture (2) and emulsified. Thus, a W/O foundation was obtained.

TABLE 5

| Components | Amount (% by mass) |
|---|---|
| 1. Cyclopentasiloxane | 9.0 |
| 2. Dimethicone | 10.0 |
| 3. Tri(caprylic acid/capric acid)glycerol | 3.0 |
| 4. PEG-10 dimethicone (note 6) | 2.0 |
| 5. Disteardimonium hectorite | 1.0 |
| 6. Zinc oxide dispersion in silicone oil (note 7) | 10.0 |
| 7. Titanium oxide dispersion in silicone oil (note 8) | 10.0 |
| 8. Liquid dispersion of titanium oxide (Example 1) | 10.0 |
| 9. Liquid dispersion of iron oxide (yellow) (Example 4) | 1.65 |
| 10. Liquid dispersion of iron oxide (red) (Example 5) | 0.55 |
| 11. Liquid dispersion of iron oxide (black) (Example 6) | 0.2 |
| 12. 1,3-Butylene glycol | 7.0 |
| 13. Citric acid Na | 0.2 |
| 14. NaCl | 0.5 |
| 15. Water | 34.9 |

(note 6)
PEG-10 dimethicone: KF-6017 (Shin-Etsu Chemical Co.)
(note 7)
Zinc oxide dispersion in silicone oil: DIF-3W4 (Sakai Chemical Industry Co., Ltd.)
(note 8)
Titanium oxide dispersion in silicone oil: DIS-12C (Sakai Chemical Industry Co., Ltd.)

The thus-obtained W/O foundation in Example 12 was stable without time-dependent changes, and the feel of the W/O foundation was smooth with good spreadability on the skin and adequate blendability with the skin when the W/O foundation was applied. The W/O foundation left no sticky or rough feeling on the skin, and exhibited excellent makeup durability.

Example 13 (W/O Foundation)

A W/O foundation was obtained by the following production method using the components shown in the following Table 6.
(Production Method)
(1) Components 6 to 9 were uniformly mixed with a portion of Component 15.
(2) Components 1 to 5 were uniformly mixed together.
(3) Components 10 to 14 and the rest of Component 15 were uniformly mixed together, and blended with the mixture (1).
(4) The mixture (3) was added to the mixture (2) and emulsified. Thus, a W/O foundation was obtained.

TABLE 6

| Components | Amount (% by mass) |
|---|---|
| 1. Cyclopentasiloxane | 19.0 |
| 2. Dimethicone | 7.0 |
| 3. Tri(caprylic acid/capric acid)glycerol | 3.0 |
| 4. Lauryl PEG-10 tris(trimethylsiloxy)silylethyl dimethicone (note 9) | 1.8 |
| 5. Disteardimonium hectorite | 0.8 |
| 6. Liquid dispersion of titanium oxide (Example 7) | 10.0 |
| 7. Liquid dispersion of iron oxide (yellow) (Example 4) | 1.65 |
| 8. Liquid dispersion of iron oxide (red) (Example 5) | 0.55 |
| 9. Liquid dispersion of iron oxide (black) (Example 6) | 0.2 |
| 10. Zinc oxide dispersion in water (note 10) | 10.0 |
| 11. Titanium oxide dispersion in water (note 11) | 10.0 |
| 12. 1,3-Butylene glycol | 5.0 |
| 13. Citric acid Na | 0.2 |
| 14. NaCl | 0.5 |
| 15. Water | 30.3 |

(note 9)
Lauryl PEG-10 tris(trimethylsiloxy)silylethyl dimethicone: ES-5300 (The Dow Chemical Company)
(note 10)
Zinc oxide dispersion in water: DIF-AB-33W (Sakai Chemical Industry Co., Ltd.)
(note 11)
Titanium oxide dispersion in water: DIS-AB-10W (Sakai Chemical Industry Co., Ltd.)

The thus-obtained W/O foundation in Example 13 was stable without time-dependent changes, and the feel of the W/O foundation was smooth with good spreadability on the skin and adequate blendability with the skin when the W/O foundation was applied. The W/O foundation left no sticky or rough feeling on the skin, and exhibited highly excellent makeup durability.

Example 14 (O/W Mascara)

An O/W mascara was obtained by the following production method using the components shown in the following Table 7.

(Production Method)

(1) Component 10 was uniformly mixed with a portion of Component 11.

(2) Components 2 to 4 and the rest of Component 11 were mixed together.

(3) Component 5 was added to the mixture (2), and Component 6 was further added thereto.

(4) Components 7 and 8 were added to the mixture (3), mixed uniformly, and heated.

(5) Component 1 that was heated was added to the mixture (4) and emulsified.

(6) Component 9 and the mixture (1) were added to the mixture (5), and mixed uniformly. Thus, an O/W mascara was obtained.

TABLE 7

| Components | Amount (% by mass) |
|---|---|
| 1. PEG-12 Carnauba | 5.0 |
| 2. Polysorbate 60 | 0.5 |
| 3. 1,3-Butylene glycol | 3.0 |
| 4. Ethanol | 4.0 |
| 5. Acrylates copolymer (Note 12) | 6.0 |
| 6. Triethanolamine | 1.0 |
| 7. Talc | 7.0 |
| 8. Polyvinyl alcohol | 0.5 |
| 9. Alkyl acrylate copolymer ammonium (note 13) | 40.0 |
| 10. Liquid dispersion of iron oxide (black) (Example 6) | 13.0 |
| 11. Water | 20.0 |

(note 12)
Acrylates copolymer: Vinysol 1050N (Daido Chemical Corporation)
(note 13)
Alkyl acrylate copolymer ammonium: Vinysol 1086WP (Daido Chemical Corporation)

The thus-obtained O/W mascara in Example 14 was stable without time-dependent changes. The feel of the O/W mascara was smooth with good spreadability and applicability to eyelashes, without stickiness. The O/W mascara exhibited excellent makeup durability.

The invention claimed is:

1. A liquid dispersion comprising:
a polyol (A);
a nonionic surfactant (B); and
40% by mass or more relative to the total 100% by mass of the liquid dispersion of a hydrophobized inorganic powder (C),
wherein the water content in 100% by mass of the liquid dispersion is 1% by mass or less,
the hydrophobized inorganic powder (C) is an inorganic powder surface-treated with at least one selected from the group consisting of silicones, alkylsilanes, fatty acids or salts thereof, amino acids or salts thereof, and alkylphosphoric acids or salts thereof, and the inorganic powder is at least one selected from the group consisting of titanium oxide, iron oxide, zinc oxide, cerium oxide, barium sulfate, calcium carbonate, silica, aluminum hydroxide, alumina, boron nitride, talc, mica, and kaolin, and
the liquid dispersion comprises 70 weight % to 95 weight % of the polyol (A) and 30 weight % to 5 weight % of the nonionic surfactant (B) relative to the total amount of the polyol (A) and the nonionic surfactant (B).

2. The liquid dispersion according to claim 1, further comprising lecithin and/or hydrogenated lecithin (D).

3. The liquid dispersion according to claim 1,
wherein the hydrophobized inorganic powder (C) has an average particle size of 150 nm to 700 nm, wherein the average particle size of the inorganic powder is a primary particle size value obtained by measuring a diameter of a minimum circumscribed circle for each of 200 particles randomly selected on a scanning electron microscope image (SEM image).

4. The liquid dispersion according to claim 1,
wherein the polyol (A) is at least one selected from the group consisting of ethylene glycol, propylene glycol, dipropylene glycol, 1,3-butylene glycol, pentylene glycol, glycerol, diglycerol, triglycerol, and polyglycerol.

5. The liquid dispersion according to claim 1,
wherein the liquid dispersion has a viscosity measured using a B-type viscometer at 25° C. of 2000 mPa·s to 500000 mPa·s.

6. A cosmetic raw material comprising:
the liquid dispersion according to claim 1.

7. A cosmetic product comprising:
the liquid dispersion according to claim 1.

* * * * *